United States Patent [19]

Jamshidi

[11] 4,266,555
[45] May 12, 1981

[54] BIOPSY NEEDLE WITH STYLET AND CANNULA ORIENTATION

[76] Inventor: Khosrow Jamshidi, 610 Winston Ct., St. Paul, Minn. 55118

[21] Appl. No.: 92,685

[22] Filed: Nov. 9, 1979

[51] Int. Cl.³ .............................................. A61B 10/00
[52] U.S. Cl. ................................... 128/753; 128/754; 128/310
[58] Field of Search ........................ 128/753, 754, 310

[56] References Cited

U.S. PATENT DOCUMENTS

| | | | |
|---|---|---|---|
| 2,496,111 | 1/1950 | Turkel | 126/754 |
| 2,850,007 | 9/1958 | Lingley | 128/754 |
| 3,001,522 | 9/1961 | Silverman | 128/754 |
| 3,175,554 | 3/1965 | Stewart | 128/754 |
| 3,598,108 | 8/1971 | Jamshidi | 128/754 |
| 3,628,524 | 12/1971 | Jamshidi | 128/754 |
| 3,995,619 | 12/1976 | Glatzer | 128/754 X |

*Primary Examiner*—Kyle L. Howell
*Attorney, Agent, or Firm*—Orrin M. Haugen; Thomas J. Nikolai

[57] ABSTRACT

An elongated hollow biopsy needle assembly which includes a cannula, a stylet arranged to be received within the cannula, a finger-gripping means, and coupling means for orienting the stylet within the cannula and for releasably securing both the cannula and the stylet to the finger-gripping means. The cannula is provided with a generally cylindrical hub which has a bore extending axially thereof, and generally in continuation with the bore of the cannula, with a conical syringe receiving counterbore being formed within the proximal end of the hub. The stylet is provided with a cap member, with the distal-facing surface of the cap being arranged to fit snugly against the proximal-facing surface of the cylindrical hub, to achieve substantially closed symmetrical mating end surfaces between the cannula and stylet, and a substantially air-tight cannula. The distal end of the cannula terminates along a plane disposed at a certain acute angle relative to the axis of the cannula, and the distal end of the stylet terminates along a plane disposed at the same angle relative to its axis. In order to achieve orientation of the stylet relative to the cannula, a groove is formed along the proximal end of the stylet, and the cap is provided with an inwardly extending tongue arranged to mate with the stylet groove, thereby achieving positive orientation of the stylet relative to the cannula.

3 Claims, 3 Drawing Figures

BIOPSY NEEDLE WITH STYLET AND CANNULA ORIENTATION

BACKGROUND OF THE INVENTION

The present invention relates generally to an improved biopsy needle, and more particularly to an elongated hollow biopsy needle assembly which is adapted to permit relatively simple disassembly, while maintaining a substantially air-tight cannula. Because of the ease of assembly and disassembly, the biopsy needle assembly of the present invention is particularly adapted for use in those situations where a disposable biopsy needle is indicated.

The present invention constitutes an improvement over those biopsy needle structures disclosed and claimed in U.S. Pat. Nos. 3,628,524 and 3,598,108, and my co-pending application entitled "BIOPSY NEEDLE HAVING INTEGRAL STYLET LOCKING DEVICE" executed on Aug. 16, 1979, as well as others. The present arrangement provides a biopsy needle assembly which is designed for ease of assembly and disassembly, and particularly with disposable needles. Provision is made to preserve both a closed symmetrical end surface between the hollow cannula and the stylet to provide a substantially air-tight cannula in the completed structure.

In the past, biopsy needles have been proposed and utilized which provide means for disassembly to facilitate sharpening, sterilization, or other routine operations. Other such structures have been provided which preserve the integrity of the structure, thereby making disassembly relatively difficult, if not impossible, with such structures having generally been designed to preserve the air-lock or air-tightness of the cannula. The present arrangement provides an improved biopsy needle assembly which is designed to permit disassembly of certain of the components, including replacement of certain of the components, particularly the needle structure. All of these features are achieved while preserving substantially an air-tight cannula.

Biopsy needles in accordance with the present invention include a cannula, a stylet which is arranged to be received within the cannula, a finger-gripping means to facilitate use, a coupling means for orienting the stylet within the cannula and for securing the cannula to the finger-gripping means along with means for orienting the stylet relative to the stylet head for achieving positive orientation of the stylet relative to the cannula. The cannula is preferably in the form of a uniform hollow cylindrical member which is provided, in the the preferred embodiment, with a bore which has a first circular diameter along the major portion of the length of the needle, and a significantly smaller circular diameter at the distal end. The internal configuration provides that specimens may be obtained without damage through crushing, thus preserving the spatial relationships of the cellular elements and organelles of tissue being biopsied. Additionally, the distal end of the cannula is formed so as to terminate along a plane which is disposed at an acute angle relative to the axis of the cannula.

The cannula is further provided with a generally cylindrical hub which has a bore extending therethrough, and which secures the proximal end of the cannula thereto. The bore formed in the hub forms an extension of the cannula bore, and a generally conical syringe-receiving counterbore is formed at the proximal end of the hub. Means are provided in the form of a flat or other radially disposed asymmetrical projection to preserve orientation of the cannula within the assembly.

The stylet is provided with an end which is generally symmetrical with the distal tip of the cannula, and a cap is secured to the proximal end. The cap is provided with a generally similar radially disposed asymmetrical projection to preserve orientation of the stylet with that of the cannula so as to provide the closed symmetrical end surface. In order to complete the orientation of the assembly, the finger-gripping means includes a generally centrally disposed coupling means with an inner surface having a radially disposed asymmetrical projections of the hub and stylet cap, with additional orientation features being present between the stylet and the stylet head.

SUMMARY OF THE INVENTION

Therefore, it is a primary object of the present invention to provide an improved biopsy needle assembly which is capable of relatively simple disassembly so as to permit expeditious replacement of the cannula, when indicated, with a substantially air-tight relationship for the cannula being preserved.

It is yet a further object of the present invention to provide an improved biopsy needle assembly which includes a cannula having a stylet arranged to be received within the cannula, with means being provided to receive a syringe within the cannula for assisting in the biopsy gathering protocol.

Other and further objects of the present invention will become apparent to those skilled in the art upon a study of the following specification, appended claims, and accompanying drawing.

IN THE DRAWING

DESCRIPTION OF THE PREFERRED EMBODIMENT

Figure 1:
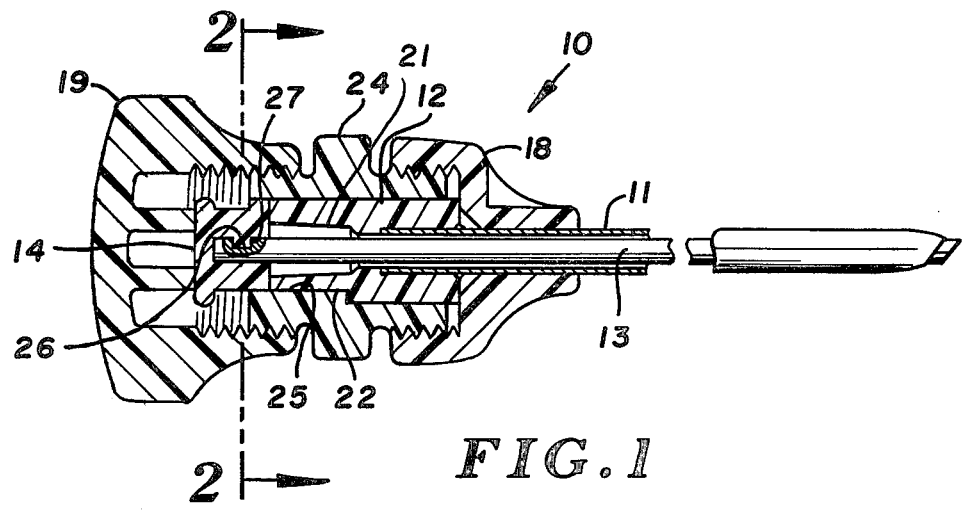
FIG. 1 is a view partially in a section taken generally through the diameter of the assembly, and illustrating the interconnecting relationships between the cannula, the stylet, and the coupling means, and with the central portion of the cannula and stylet being cut away so as to include a view of the distal tip end of the structure.

In accordance with the preferred embodiment of the present invention, the biopsy needle assembly generally designated 10 includes a hollow cannula 11 to which there is secured a generally cylindrical hub 12. Hub 12 has distal and proximal facing end surfaces. A stylet is provided as at 13, with the stylet having a configuration which is substantially similar to and arranged to fit within the internal diameter of the cannula. A stylet cap is provided as at 14, with the distal-facing surface of cap 14 being machined so as to fit snugly against the proximal-facing surface 16 of the hub 12. A cannula retainer is provided at 18, with a stylet retainer and closed cap element being provided as at 19. Cap 19 has distal and proximal facing end surfaces.

With attention now being directed to the substance of the cannula 11, it will be noted that the internal diameter of cannula 11 is arranged so that there is an internal taper adjacent the distal end. In other words, the needle converges from a first circular diameter which extends along the major portion of the length of the needle toward and to a second and significantly smaller circular diameter at the distal end. Also, the cannula tip as at 20 terminates along a plane disposed at approximately 45° relative to the axis, so as to be provided with an angular cutting face. This arrangement permits and facilitates radial cutting when the needle is revolved about its longitudinal axis. In certain configurations, it may be desirable to form a scallop pattern so as to permit ease of penetration of bone, depending upon the specific procedure or protocol indicated.

The cannula is provided with a generally cylindrical hub member at the proximal end of the cannula, with the hub having a bore which extends generally axially therethrough, and in continuation with the bore of the hollow cannula. The hub secures the proximal end of the cannula to the inner diameter thereof, with the hub further having a conical syringe receiving counterbore formed therein generally as at 21. This arrangement permits the insertion and coupling of a conventional plastic syringe thereto, such as the syringe disclosed and claimed in U.S. Pat. No. 4,022,191, for example.

The stylet 13 is provided with an outer configuration which is substantially similar to and matching the inner configuration of the cannula 11. Specifically, the distal tip of the stylet is tapered so as to substantially match the converging taper of the cannula. At the proximal end of the stylet, a cap 14 is provided which has an inner surface 17 which substantially matches and fits snugly against the proximal-facing surface 16 of hub 12.

Both cylindrical hub 12 and stylet cap 14 are provided with radially disposed asymmetrical orientation surfaces. Specifically, a flat is formed in the proximal end of hub 12, as at 22, and a matching flat is formed in stylet cap 14 as at 23. Both flats are arranged to mate with a corresponding flat formed in the bore of coupling means 24. In other words, coupling means 24 has a bore extending therethrough, into which cylindrical hub 12 and stylet cap 14 are received, with a corresponding or mating flat zone being provided as at 25. The arrangement of flat zones has been found to preserve the orientations so that the stylet and cannula provide a closed symmetrical end surface, with the flats further providing a substantially air-tight cannula structure.

Figure 2:
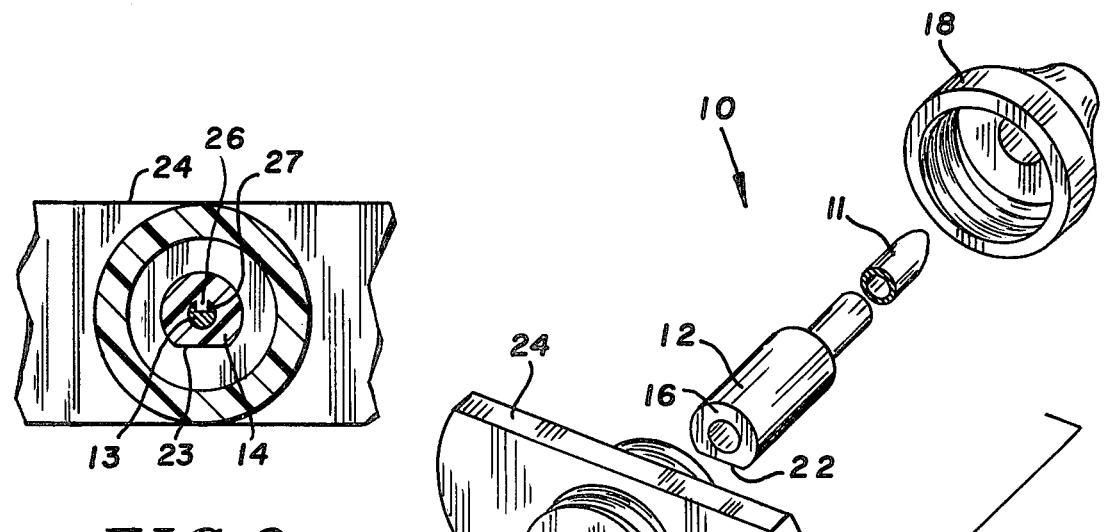
FIG. 2 is a sectional view taken along the line and in the direction of the arrows 2—2 of FIG. 1.
Figure 3:
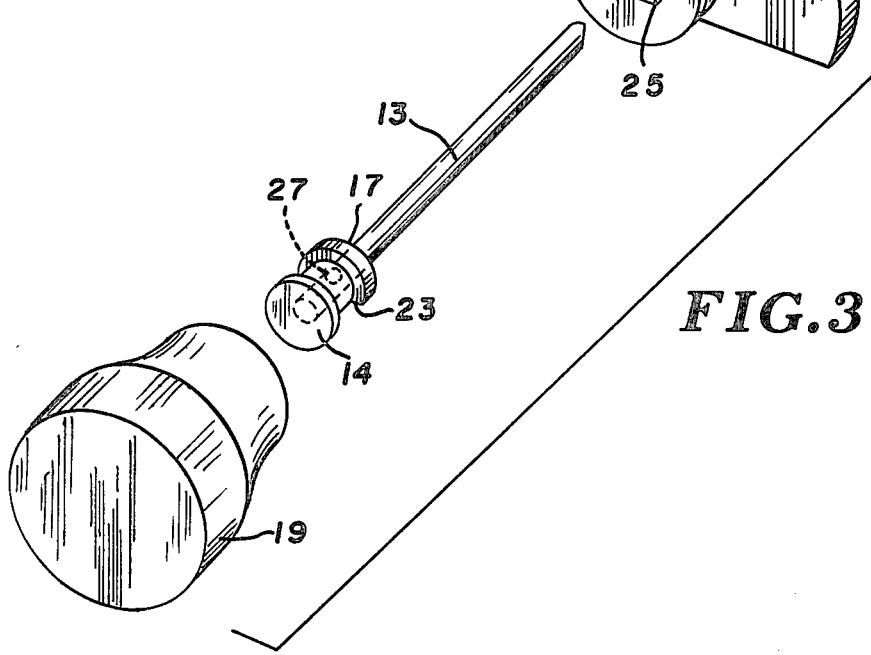
FIG. 3 is an exploded perspective view of the assembly.

With particular attention being directed to the detailed showing of FIGS. 1 and 2, it will be noted that the stylet cap 14 is provided with an inwardly extending tongue element as at 26, with a tongue-receiving groove being formed within stylet 13, as at 27. The combination of the tongue and groove 26 and 27 preserves the angular orientation of stylet 13 relative to cannula 11.

In order to disassemble the arrangement, stylet retainer 19 is removed, thus permitting the withdrawal of the cannula 11 from the coupling means 24. Removal of stylet retainer 19 will permit the stylet to be removed from the assembly. The individual components are normally formed of medically acceptable materials of construction, and the needle portion may be formed so as to be susceptible of a one-time use, if desired, or alternatively fabricated of a medically acceptable material which may be treated for subsequent application and operation.

The techniques employed in the use of this structure are straight forward and well known. The stylet is inserted into the cannula, and interlocked therewith as indicated. The needle structure may be inserted into the patients body until the tissue to be removed is engaged with the distal end tip of the needle. In the event that a bone marrow sample is to be obtained, a rasp-like surface or scalloped surface at the distal end of the cannula will facilitate penetration of the bone. Rotation of the needle about its longitudinal axis will produce a boring effect upon the bone and facilitates entry of the structure into the marrow. When the distal end of the needle has reached the tissue from which the specimen is to be removed, the stylet 13 is removed from the needle and the needle is again rotated about its longitudinal axis while it is urged forwardly. This movement of the needle produces a cutting action of the tissue to be removed, and allows the specimen to be collected interiorly of the needle. Because of the expanded configuration of the interior of the tapered portion, the biopsy specimen gathered will not be crushed.

As an alternate procedure, an aspirating system may be employed wherein the hub of a syringe is inserted into the conical counterbore 21, with aspiration of the syringe being employed to draw tissue or body fluids into the distal tip end of the needle.

In certain embodiments, it is desirable to provide a cutting edge for the cannula in which a pair of diametrically opposed teeth may be utilized for cutting certain tissue. A rasp-like exterior surface may be employed in needles which are designed to be used in obtaining bone and/or bone marrow biopsy specimens. The structure of the present invention is, of course, capable of use in connection with any of these proposed applications or operations.

I claim:

1. An elongated hollow biopsy needle assembly with open distal and proximal ends, and with the distal end defining a cutting edge, said assembly including a cannula, an elongated stylet removably received within the bore of said cannula, a finger gripping means, and coupling means for orienting said stylet within said cannula and for releasably securing said cannula to said finger gripping means.

(a) said cannula being of uniform hollow, cylindrical configuration throughout the major portion of its length and having an external distal end surface tapered generally uniformly, uninterrupted, toward the tip of the distal end, and an internal end surface defining an inner biopsy tissue receiving and retaining bore immediately adjacent the distal end and with the distal end of said cannula terminating along a plane disposed at a certain acute angle relative to the axis of said cannula;

(b) a generally cylindrical hub having a bore extending axially therethrough and securing the proximal end of said cannula to the inner diameter thereof, and with the bore of said hub forming an extension of the hollow cannula, a conical syringe receiving counterbore formed within the proximal end of said hub, and a radially disposed asymmetrical orientation surface formed along an end of said hub;

(c) said elongated stylet being positioned within said cannula and corresponding generally in length and shape to the bore formed in said cannula, and having a distal end terminating along a plane disposed at said certain acute angle relative to the axis thereof, said stylet further having a cap secured to the proximal end thereof with said cap having a radially disposed asymmetrical orientation surface formed along the outer surface thereof, and with said stylet having a groove formed along the proximal end thereof and with said cap having a tongue extending radially inwardly and arranged to mate with said groove for orienting said stylet relative to said cap;

(d) said finger gripping means including a generally centrally disposed coupling means with an inner surface having a radially extending asymmetrical surface mating with the radially disposed asymmetrical orientation surfaces of each of said cylindrical hub and said stylet for orienting said cannula relative to said stylet cap to present a closed symmetrical end surface.

2. The biopsy needle assembly as defined in claim 1 being particularly characterized in that the distal facing end surface of said stylet cap fits snugly against the proximal facing end of said cylindrical hub.

3. The biopsy needle assembly as defined in claim 1 being particularly characterized in that the internal diameter of said cannula has an inwardly directed taper extending from a point adjacent said distal end toward and to the distal end thereof.

* * * * *

UNITED STATES PATENT AND TRADEMARK OFFICE
CERTIFICATE OF CORRECTION

PATENT NO. : 4,266,555
DATED : May 12, 1981
INVENTOR(S) : Khosrow Jamshidi

It is certified that error appears in the above–identified patent and that said Letters Patent are hereby corrected as shown below:

Column 5, line 10, after "stylet" insert -- cap --.

Column 6, line 1, delete the word "cap".

*Signed and Sealed this*

*Twenty-eighth* Day of *July 1981*

[SEAL]

*Attest:*

*Attesting Officer*

GERALD J. MOSSINGHOFF

*Commissioner of Patents and Trademarks*